United States Patent
Lin et al.

(10) Patent No.: US 8,936,804 B2
(45) Date of Patent: *Jan. 20, 2015

(54) USE OF VANADIUM COMPOUNDS TO ACCELERATE BONE HEALING

(75) Inventors: Sheldon Suton Lin, Chatham, NJ (US); David Naisby Paglia, New Britain, CT (US); James Patrick O'Connor, Fanwood, NJ (US); Eric Breitbart, South Orange, NJ (US); Joseph Benevenia, Montclair, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 98 days.

This patent is subject to a terminal disclaimer.

(21) Appl. No.: 13/522,075

(22) PCT Filed: Jan. 14, 2011

(86) PCT No.: PCT/US2011/021296
§ 371 (c)(1),
(2), (4) Date: Feb. 12, 2013

(87) PCT Pub. No.: WO2011/088318
PCT Pub. Date: Jul. 21, 2011

(65) Prior Publication Data
US 2013/0171094 A1    Jul. 4, 2013

Related U.S. Application Data

(60) Provisional application No. 61/295,234, filed on Jan. 15, 2010.

(51) Int. Cl.
*A61K 38/00* (2006.01)
*A61K 38/16* (2006.01)
(Continued)

(52) U.S. Cl.
CPC .............. *A61K 31/555* (2013.01); *A61K 38/00* (2013.01); *A61K 9/0024* (2013.01);
(Continued)

(58) Field of Classification Search
None
See application file for complete search history.

(56) References Cited

U.S. PATENT DOCUMENTS

| 5,019,383 | A | 5/1991 | Hopp |
| 5,061,286 | A | 10/1991 | Lyle |

(Continued)

FOREIGN PATENT DOCUMENTS

| DE | 10238161 A1 | 2/2004 |
| WO | 96/36333 A1 | 11/1996 |

(Continued)

OTHER PUBLICATIONS

Barrio et al. (2006, Can. J. Physiol. Pharmacol. 84:667-686).*

(Continued)

*Primary Examiner* — Elizabeth C Kemmerer
(74) *Attorney, Agent, or Firm* — Fox Rothschild LLP (57) ABSTRACT

This invention provides a method of promoting bone healing by locally administering a vanadium-based insulin mimetic agent to a patient in need thereof. The invention also provides a new use of insulin-mimetic vanadium compounds for manufacture of medicaments for accelerating bone-healing processes. In addition, the invention also encompasses a bone injury treatment kit suitable for localized administration of insulin-mimetic vanadium compounds or compositions thereof to a patient in need of such treatment.

26 Claims, 5 Drawing Sheets

(51) Int. Cl.
*A61K 38/17* (2006.01)
*A61K 38/18* (2006.01)
*A61K 38/19* (2006.01)
*A61K 38/22* (2006.01)
*A61K 38/29* (2006.01)
*C22C 27/02* (2006.01)
*A61K 9/00* (2006.01)
*A61K 31/555* (2006.01)
*A61K 33/24* (2006.01)
*A61K 45/06* (2006.01)
*A61K 31/661* (2006.01)
*A61L 27/54* (2006.01)

(52) U.S. Cl.
CPC ....... *A61L 2300/102* (2013.01); *A61L 2300/45* (2013.01); *A61K 9/0019* (2013.01); *A61L 2430/02* (2013.01); *A61K 33/24* (2013.01); *A61K 45/06* (2013.01); *A61K 31/661* (2013.01); *A61L 27/54* (2013.01)
USPC .......... 424/422; 420/424; 422/423; 514/16.7; 514/7.6; 514/8.1; 514/8.2; 514/8.5; 514/8.6; 514/8.8; 514/8.9; 514/9.1; 514/9.7; 514/11.8

(56) References Cited

U.S. PATENT DOCUMENTS

| | | | |
|---|---|---|---|
| 5,716,415 | A | 2/1998 | Steffee |
| 5,871,779 | A | 2/1999 | Cruz |
| 7,763,582 | B2 | 7/2010 | Lin et al. |
| 2003/0211170 | A1 | 11/2003 | Gho |
| 2004/0019132 | A1 | 1/2004 | Long et al. |
| 2004/0121025 | A1 | 6/2004 | McKee |
| 2004/0230309 | A1 | 11/2004 | DiMauro et al. |
| 2004/0242953 | A1 | 12/2004 | Good |
| 2006/0051397 | A1 | 3/2006 | Maier et al. |
| 2006/0093646 | A1 | 5/2006 | Cima et al. |
| 2006/0183729 | A1 | 8/2006 | Uckun |
| 2007/0027543 | A1 | 2/2007 | Gimble et al. |
| 2007/0073385 | A1 | 3/2007 | Schaeffer et al. |
| 2007/0181433 | A1 | 8/2007 | Birdsall et al. |
| 2008/0248636 | A1 | 10/2008 | Olander et al. |
| 2009/0104095 | A1 | 4/2009 | Morgan et al. |
| 2009/0214468 | A1 | 8/2009 | Lin et al. |
| 2010/0168854 | A1 | 7/2010 | Luers et al. |
| 2010/0211158 | A1 | 8/2010 | Haverty et al. |
| 2010/0226943 | A1 | 9/2010 | Brennan et al. |
| 2011/0004307 | A1 | 1/2011 | Ahn et al. |

FOREIGN PATENT DOCUMENTS

| | | |
|---|---|---|
| WO | 00/24730 A1 | 5/2000 |
| WO | 2012/079024 A2 | 6/2012 |
| WO | 2013082295 A1 | 6/2013 |

OTHER PUBLICATIONS

Barrio et al. "Vanadium and bone development: putative signaling pathways", Journal of the All-India Ophthalmological Society 84(7): 677-686. (2006).

Barrio et al. "Potential use of vanadium compounds in therapeutics", Current Medicinal Chemistry 17(31): 3632-3642. (2010).

Arai Michitsugu: "Effects of vanadyl sulfate on osteopenia in streptozotocin-induced diabetic (STZD) rats: Comparison with those of insulin", Folia Pharmacologica Japonica 100(5): 401-414. (1992).

Facchini et al. "The effects of vanadium treatment on bone in diabetic and non-diabetic rats", Bone 38(3): 368-377. (2006).

Cortizo et al. "Osteogenic activity of vanadyl(IV)-ascorbate complex: Evaluation of its mechanism of action", International Journal of Biochemistry and Cell Biology 38(7): 1171-1180. (2006).

Paglia et al. "The effects of local vanadium treatment on angiogenesis and chondrogenesis during fracture healing", Journal of Orthopaedic Research 30(12): 1971-1978. (2012).

Barrio et al., Vanadium and bone development: putative signaling pathways, Can. J. Physiol. Pharmacol., vol. 84, No. 7, p. 677-686. (Jul. 2006).

Mehdi et al., "Organo-vanadium compounds are potent activators of the protein kinase B signaling pathway and protein tyrosine phosphorylation: Mechanism of insulinomimesis," Arch. Biochem. Biophys., vol. 440, No. 2, p. 158-164. (Aug. 15, 2005).

Millard D. J. Wound Care 4(8):343, 1995.

Kagel EM, et al. Current Opinion in Orthopaedics 6(5):7-13, 1995.

Wildemann B, et al. Bone (34):862-868, 2004.

Cornish, J. et al., Insulin Increases Histomorphometric Indices of Bone Formation in Vivo, Calcif Tissue Intl, 1996, 59:492-495.

Gandhi, A. et al., The Effects of Local Insulin Delivery on Diabetic Fracture Healing, Bone, 2005, pp. 482-490.

Stuck, Walter G., The Effect of Insulin on the Healing of Experimental Fractures in the Rabbit, J. Bone Joint Surg Am., 1932, 14:109-115.

* cited by examiner

USE OF VANADIUM COMPOUNDS TO ACCELERATE BONE HEALING

CROSS-REFERENCE TO RELATED APPLICATIONS

This application is a U.S. national stage application of International Application No. PCT/US2011/021296, filed on Jan. 14, 2010, which claims priority under 35 U.S.C. §119(e) to U.S. Provisional Patent Application Ser. No 61/295,234, filed on Jan. 15, 2010, both of which are hereby incorporated by reference in their entirety.

FIELD OF THE INVENTION

The present invention relates to a novel method for bone healing in patients by local administration of insulin-mimetic vanadium compounds as anabolic agents. The invention encompasses methods for treatment of bone injuries with insulin-mimetic vanadium compounds or compositions thereof and use of insulin-mimetic vanadium compounds for manufacture of medicaments for treatment of bone injuries, as well as bone injury treatment kits suitable for local administration of insulin-mimetic vanadium compounds.

BACKGROUND OF THE INVENTION

About six million bone fractures, including about 600,000 non-union cases, occur annually in the United States, among which approximately 10% do not heal. In the orthopedic procedures conducted, about one million performed annually require allograft or autograft. One solution to enhancement of bone healing is through tissue engineering, in which cells, such as osteoblast, fibroblast, chondroblasts, are treated with bioactive signaling molecules, e.g., insulin or insulin mimetics or Scaffolds such as β-TCP (tricalcium phosphate) and collagen under an appropriate environment. Current methods of treatment of bone fractures include (a) electro-stimulation devices (such as PEMF, Exogen) and (b) biologics, such as bone morphogenic proteins (BMPs), e.g., rhBMP-2/ACS (INFUSE® Bone Graft). The latter has been approved by FDA as an autograft replacement in spine fusion (ALIF) with specific interbody cages (2002), as an adjuvant for repair of tibia fractures with IM nail (2004), and for craniofacial maxillary surgery (2006), but this method is expensive, costing about $5,000 per application. (Lieberman, J. R., et al., *J. Bone Joint Surg. Am.*, 2002, 84: 1032-1044; Trippel, S. B., et al., *J. Bone Joint Surg. Am.*, 1996, 78: 1272-86.)

Fracture healing is a complex process that involves the sequential recruitment of cells and the specific temporal expression of factors essential for bone repair. The fracture healing process begins with the initial formation of a blood clot at the fracture site. Platelets and inflammatory cells within the clot release several factors that are important for chemotaxis, proliferation, angiogenesis and differentiation of mesenchymal cells into osteoblasts or chondroblasts.

The fracture healing process subsequent to the initial hematoma formation can be classified as primary or secondary fracture healing. Primary fracture healing occurs in the presence of rigid internal fixation with little to no interfragmentary strain resulting in direct bone formation across the fracture gap. Secondary fracture healing occurs in response to interfragmentary strain due to an absence of fixation or non-rigid fixation resulting in bone formation through intramembranous and endochondral ossification characterized by responses from the periosteum and external soft tissue.

Intramembranous bone formation originates in the periosteum. Osteoblasts located within this area produce bone matrix and synthesize growth factors, which recruit additional cells to the site. Soon after the initiation of intramembranous ossification, the granulation tissue directly adjacent to the fracture site is replaced by cartilage leading to endochondral bone formation. The cartilage temporarily bridging the fracture gap is produced by differentiation of mesenchymal cells into chondrocytes. The cartilaginous callus begins with proliferative chondrocytes and eventually becomes dominated by hypertrophic chondrocytes. Hypertrophic chondrocytes initiate angiogenesis and the resulting vasculature provides a conduit for the recruitment of osteoblastic progenitors as well as chondroclasts and osteoclasts to resorb the calcified tissue. The osteoblastic progenitors differentiate into osteoblasts and produce woven bone, thereby forming a united fracture. The final stages of fracture healing are characterized by remodeling of woven bone to form a structure, which resembles the original tissue and has the mechanical integrity of unfractured bone.

However, the processes of bone metabolism are vastly different from bone repair. Bone metabolism is the interplay between bone formation and bone resorption. Bone repair, as described previously, is a complex process that involves the sequential recruitment and the differentiation of mesenchymal cells towards the appropriate osteoblastic/chondrogenic lineage to repair the fracture/defect site.

SUMMARY OF THE INVENTION

The present invention provides unique strategies for bone healing through local administration of vanadium compounds as anabolic agents.

In one aspect the present invention provides a method of treating a bone condition in a patient in need thereof, comprising locally administering to the patient a therapeutically effective amount of an insulin-mimetic vanadium compound.

In another aspect the present invention provides a method of treating a bone condition in a patient in need thereof, comprising locally administering to the patient a therapeutically effective amount of a composition comprising an insulin-mimetic vanadium compound.

In another aspect the present invention provides use of an insulin-mimetic vanadium compound for manufacture of a medicament for accelerating bone healing in a patient in need thereof characterized by local administration of said medicament.

Preferably, the patient in need of bone healing is afflicted with a bone condition selected from bone fracture, bone trauma, arthrodesis, and a bone deficit condition associated with post-traumatic bone surgery, post-prosthetic joint surgery, post-plastic bone surgery, post-dental surgery, bone chemotherapy treatment, congenital bone loss, post traumatic bone loss, post surgical bone loss, post infectious bone loss, allograft incorporation or bone radiotherapy treatment. More preferably, the bone condition is a bone fracture.

Preferably, the vanadium compound is an insulin mimetic organovanadium compound, such as vanadium compounds used for vanadium-based drugs vanadyl acetylacetonate and bis(ethylmaltolato)oxovanadium(IV), which are insulin mimetic and have not been described for bone healing and fracture repair. Other preferred vanadium compounds also include, but are not limited to, vanadyl sulfate (VS), vanadyl 3-ethylacetylacetonate (VET), and vanadyl(IV) ascorbate complexes.

A more preferred vanadium compound for the present invention is vanadyl acetylacetonate (VAC), an organovanadium compound that has demonstrated insulin-mimetic effects in type 1 and type 2 diabetic animals and human studies, e.g., preventing some of the associated complications of diabetes in animal studies.

Additional pharmacological activities of VAC that have been studied include inhibition of gluconeogenesis, a decrease in glutamate dehydrogenase activity, and antipolysis.

An additional aspect of the present invention provides a drug delivery device or kit, which includes an insulin-mimetic vanadium compound and a pharmaceutically acceptable carrier, wherein the device or kit is adapted for localized administration of the vanadium compound to a patient in need thereof. Localized delivery of vanadium-based insulin mimetics significantly enhanced biomechanical properties in 4 weeks, and the outcome is dosage dependent, with lower dosages giving superior results.

Another additional aspect of the present invention includes localized administration of a vanadium compound or a composition thereof in conjunction with treating the patient with at least one additional procedure selected from bone autograft, bone allograft, autologous stem cell treatment, allogeneic stem cell treatment, chemical stimulation, electrical stimulation, internal fixation, and external fixation.

The present invention thus provides a unique method for promoting bone healing in a patient, preferably mammalian animal and more preferably a human, either diabetic or non-diabetic. Development of a vanadium therapy of the present invention would obviate the need for developing specialized methods to deliver growth factors and thereby reduce costs associated with therapy, eliminate specialized storage, and enhance ease of use. These and other aspects of the present invention will be better appreciated by reference to the following drawings and detailed description.

BRIEF DESCRIPTION OF THE DRAWINGS

FIG. 2 shows Mechanical Testing Setup: (A) intact femur before embedded in ¾ inch square nut with Field's Metal, (B) intact femur embedded in hex nut and mounted in the mechanical testing apparatus, (C) intact femur mounted in the mechanical testing apparatus after torsional testing, (D) intact femur after torsional testing, (E) fractured femur after torsional testing showing spiral fracture indicative of healing, and (F) fractured femur after torsional testing showing non-spiral fracture indicative of non-union.

FIG. 5 shows spiral fractures after testing.

DETAILED DESCRIPTION OF THE INVENTION

The present invention is based on a hypothesis that vanadium can be used to accelerate bone regeneration by stimulating insulin pathway signaling at a fracture site. In exploiting the biological impact of vanadium as an insulin-mimetic agent on bone, the present inventors found that these agents play a critical role in bone healing. The present invention thus uses an insulin-mimetic vanadium-based compound to treat various bone conditions, in particular, bone fractures.

In one aspect the present invention provides a method of treating a bone condition in a patient in need thereof, comprising locally administering to the patient a therapeutically effective amount of an insulin-mimetic vanadium compound.

In one embodiment of this aspect, the present invention provides a method of treating a bone condition in a patient, wherein the insulin-mimetic vanadium compound is an organovanadium compound selected from the group consisting of vanadyl acetylacetonate (VAC), vanadyl sulfate (VS), vanadyl 3-ethylacetylacetonate (VET), and bis(maltolato)oxovanadium (BMOV).

In a preferred embodiment of this aspect, the present invention provides a method of treating a bone condition in a patient, wherein the insulin-mimetic vanadium compound is vanadyl acetylacetonate (VAC).

In another embodiment of this aspect, the present invention provides a method of treating a bone condition in a patient, wherein the insulin-mimetic vanadium compound is directly administered to the bone injury site.

Preferably, the patient in need of bone healing is afflicted with a bone condition selected from bone fracture, bone trauma, arthrodesis, and a bone deficit condition associated with post-traumatic bone surgery, post-prosthetic joint surgery, post-plastic bone surgery, post-dental surgery, bone chemotherapy treatment, congenital bone loss, post traumatic bone loss, post surgical bone loss, post infectious bone loss, allograft incorporation or bone radiotherapy treatment.

In another embodiment of this aspect, the present invention provides a method of treating a bone condition in a patient, wherein the bone condition is selected from bone fractures, osseous defects, and delayed unions and non-unions.

In another embodiment of this aspect, the present invention provides a method of treating a bone condition in a patient, wherein the method is used in conjunction with an allograft/autograft or orthopedic biocomposite.

In another embodiment of this aspect, the present invention provides a method of treating a bone condition in a patient, wherein said insulin-mimetic vanadium compound is locally administered by a bone graft biocomposite containing said insulin-mimetic vanadium compound.

In another embodiment, the present invention provides a method of treating a bone condition in a patient, wherein the bone graft biocomposite is selected from the group consisting of autografts, allografts, xenografts, alloplastic grafts, and synthetic grafts. In a preferred embodiment, the bone graft is selected from the group consisting of autografts and allografts.

In another embodiment of this aspect, the present invention provides a method of treating a bone condition in a patient, wherein the method comprises co-administering a cytotoxic agent, cytokine or growth inhibitory agent with said vanadium compound.

In another embodiment of this aspect, the present invention provides a method of treating a bone condition in a patient, wherein the method is used in conjunction with an external bone growth stimulator, for example, Exogen and Pulsed Electro Magnetic Field Therapy (PEMF).

In another embodiment of this aspect, the present invention provides a method of treating a bone condition in a patient, wherein the method co-administering a bioactive bone agent with said vanadium compound.

In another embodiment of this aspect, the present invention provides a method of treating a bone condition in a patient, wherein the method is used in conjunction with administration of a bioactive bone agent selected from the group consisting of peptide growth factors, anti-inflammatory factors, pro-inflammatory factors, inhibitors of apoptosis, MMP inhibitors, and bone catabolic antagonists.

In another embodiment of this aspect, the present invention provides a method of treating a bone condition in a patient, wherein the method is used in conjunction with administration of a peptide growth factor selected from the group consisting of IGF (1,2), PDGF (AA, AB, BB), BMPs, FGF (1-20), TGF-beta (1-3), aFGF, bFGF, EGF, VEGF, parathyroid hormone (PTH), and parathyroid hormone-related protein (PTHrP).

In another embodiment of this aspect, the present invention provides a method of treating a bone condition in a patient, wherein the method is used in conjunction with administration of an anti-inflammatory factor selected from the group consisting of anti-TNFa, soluble TNF receptors, IL1ra, soluble IL1 receptors, IL4, IL-10, and IL-13.

In another embodiment of this aspect, the present invention provides a method of treating a bone condition in a patient, wherein the method is used in conjunction with administration of a bone catabolic antagonist selected from the group consisting of bisphosphonates, osteoprotegerin, and statins.

In another embodiment of this aspect, the present invention provides a method of treating a bone condition in a patient, wherein the patient is a mammalian animal.

In another embodiment of this aspect, the present invention provides a method of treating a bone condition in a patient, wherein the patient is a human.

In another embodiment of this aspect, the present invention provides a method of treating a bone condition in a patient, wherein the patient is a non-diabetic human.

In another aspect, the present invention provides a method of treating a bone condition in a patient, comprising locally administering to the patient a therapeutically effective amount of a composition comprising an insulin-mimetic vanadium compound.

In one embodiment of this aspect, the present invention provides a method of treating a bone condition in a patient, wherein the insulin-mimetic vanadium compound is an organovanadium compound.

In another embodiment of this aspect, the present invention provides a method of treating a bone condition in a patient, wherein the composition further comprises at least one biocompatible carrier.

In another embodiment of this aspect, the present invention provides a method of treating a bone condition in a patient, wherein the composition further comprises at least one biocompatible carrier selected from the group consisting of poly-lactic acid, poly-glycolic acid, and copolymers of poly-lactic acid and poly-glycolic acid.

In another embodiment of this aspect, the present invention provides a method of treating a bone condition in a patient, wherein the composition further comprises at least one biocompatible carrier selected from the group consisting of biodegradable fatty acids and metal salts of fatty acids.

In another embodiment of this aspect, the present invention provides a method of treating a bone condition in a patient, wherein the composition further comprises at least one biocompatible carrier selected from the group consisting of palmitic acid, stearic acid, oleic acid, myristic acid, and metal salts thereof.

In another embodiment of this aspect, the present invention provides a method of treating a bone condition in a patient, wherein the composition further comprises at least one biocompatible carrier selected from the group consisting of porous or non-porous calcium phosphates, porous or non-porous hydroxyapatites, porous or non-porous tricalcium phosphates, porous or non-porous tetracalcium phosphates, and porous or non-porous calcium sulfates, or a combination thereof.

In another embodiment of this aspect, the present invention provides a method of treating a bone condition in a patient, comprising locally administering to the patient a therapeutically effective amount of a composition comprising a vanadium compound and further comprising treating said patient with at least one procedure selected from the group consisting of bone autograft, bone allograft, autologous stem cell treatment, allogeneic stem cell treatment, chemical stimulation, electrical stimulation, internal fixation, and external fixation.

In another aspect the present invention provides use of an insulin-mimetic vanadium compound for manufacture of a medicament for accelerating bone healing in a patient in need thereof characterized by local administration of said medicament.

Preferably, the patient in need of bone healing is afflicted with a bone condition selected from bone fracture, bone trauma, arthrodesis, and a bone deficit condition associated with post-traumatic bone surgery, post-prosthetic joint surgery, post-plastic bone surgery, post-dental surgery, bone chemotherapy treatment, congenital bone loss, post traumatic bone loss, post surgical bone loss, post infectious bone loss, allograft incorporation or bone radiotherapy treatment.

In one embodiment of this aspect the present invention provides use of a vanadium compound for manufacture of a medicament for accelerating bone healing in a patient in need thereof characterized by local administration of said medicament, wherein the insulin-mimetic vanadium compound is an inorganic vanadium compound.

In another embodiment of this aspect the present invention provides use of a vanadium compound for manufacture of a medicament for accelerating bone healing in a patient in need thereof characterized by local administration of said medicament, wherein the insulin-mimetic vanadium compound is an organovanadium compound.

In one preferred embodiment of this aspect the present invention provides use of a vanadium compound for manufacture of a medicament for accelerating bone healing in a patient in need thereof characterized by local administration of said medicament, wherein the insulin-mimetic vanadium compound is an organovanadium compound selected from the group consisting of vanadyl acetylacetonate (VAC), vanadyl sulfate (VS), vanadyl 3-ethylacetylacetonate (VET), and bis(maltolato)oxovanadium (BMOV).

In another aspect the present invention provides a bone injury treatment kit comprising a therapeutically effective amount of an insulin-mimetic vanadium compound formulated for localized administration of said vanadium compound to a patient in need thereof.

In one embodiment of this aspect the present invention provides a bone injury treatment kit, wherein the insulin-mimetic vanadium compound is an organovanadium compound.

In another embodiment of this aspect the present invention provides a bone injury treatment kit, wherein the insulin-mimetic vanadium compound is selected from the group consisting of vanadyl acetylacetonate (VAC), vanadyl sulfate (VS), vanadyl 3-ethylacetylacetonate (VET), and bis(maltolato)oxovanadium (BMOV).

In another embodiment of this aspect the present invention provides a bone injury treatment kit, wherein the insulin-mimetic vanadium compound is vanadyl acetylacetonate (VAC).

In another embodiment of this aspect the present invention provides a bone injury treatment kit, wherein the patient is a mammalian animal.

In another embodiment of this aspect the present invention provides a bone injury treatment kit, wherein the patient is a human.

In another embodiment of this aspect the present invention provides a bone injury treatment kit, wherein the patient is a non-diabetic human.

In another embodiment of this aspect the present invention provides a bone injury treatment kit, wherein the patient is an animal selected from horses, dogs, and cats.

In another embodiment of this aspect the present invention provides a bone injury treatment kit, further comprising a bone graft biocomposite.

In another embodiment of this aspect the present invention provides a bone injury treatment kit, further comprising a bioactive agent for treating injured bone tissue.

Preferred sites of interest in the patient include sites in need of bone healing and areas adjacent and/or contiguous to these sites. Optionally, the treatment method of the present invention is combined with at least one procedure selected from bone autograft, bone allograft, autologous stem cell treatment, allogeneic stem cell treatment, chemical stimulation, electrical stimulation, internal fixation, and external fixation.

The vanadium compounds of the invention can be any organic vanadium compound known to increase safety, improve absorption, and reduce undesirable side effects associated with therapeutic vanadium, for example, vanadyl sulfate (VS), vanadyl 3-ethylacetylacetonate (VET), bis(maltolato)oxovanadium (BMOV), and vanadyl acetylacetonate (VAC).

Advantages of an insulin mimetic include, but are not limited to: (a) development of a small molecule insulin mimetic can be of great significance to bone fracture patients; (b) insulin composite which requires a carrier may be difficult to meet FDA requirements as a dual agent product; and (c) vanadium salts may have longer half life and avoid the storage issues commonly seen with proteins.

Vanadium, which exists in +4 (vanadyl) and +5 (vanadate) compounds in the biological body, have demonstrated poor absorption rates within the gastrointestinal (GI) tract and GI side-effects, such as diarrhea and vomiting. As a result, additional organic vanadium compounds, i.e., vanadyl sulfate (VS), vanadyl 3-ethylacetylacetonate (VET), bis(maltolato) oxovanadium (BMOV), and VAC, have been synthesized in order to improve absorption and safety (Poucheret, P., et al., Mol. Cell Biochem., 1998, 188(1-2): 73-80). VAC with an organic ligand has been proven to be more effective in its anti-diabetic function compared with other vanadium compounds, including BMOV, VS, and VET (Reul, B. A., et al., Br. J. Pharmacol. 1999, 126(2):467-477). Unfortunately, in these studies the concentration and doses of the vanadium complexes were not closely regulated to the exact dosage required to obtain insulin-mimetic effects remain unclear. The doses delivered in the present study are closely regulated and evaluated at various time points. Our lab demonstrated full animal survivorship at 4 weeks with no indication of sickness, diarrhea, or vomiting after a single local dose administration suggest the safety of this treatment.

Exemplary healing mechanisms include, but are not limited to: (a) retaining mineralized components in bone, (b) inhibiting release of mineralized components from bone, (c) stimulating osteoblast activity, (d) reducing osteoclast activity, or (e) stimulating bone remodeling.

The term "therapeutically effective amount," as used herein, means an amount at which the administration of an agent is physiologically significant. The administration of an agent is physiologically significant if its presence results in a detectable change in the bone healing process of the patient.

The term "bone injury," "injured bone," or the like, as used herein, refers to a bone condition selected from the group consisting of bone fracture, bone trauma, arthrodesis, and a bone deficit condition associated with post-traumatic bone surgery, post-prosthetic joint surgery, post-plastic bone surgery, post-dental surgery, bone chemotherapy treatment, congenital bone loss, post traumatic bone loss, post surgical bone loss, post infectious bone loss, allograft incorporation or bone radiotherapy treatment.

It will be appreciated that actual preferred amounts of a pharmaceutical composition used in a given therapy will vary depending upon the particular form being utilized, the particular compositions formulated, the mode of application, and the particular site of administration, and other such factors that are recognized by those skilled in the art including the attendant physician or veterinarian. Optimal administration rates for a given protocol of administration can be readily determined by those skilled in the art using conventional dosage determination tests.

Dosages of a vanadium compound employable with the present invention may vary depending on the particular use envisioned. The determination of the appropriate dosage or route of administration is well within the skill of an ordinary physician.

For example, when in vivo administration of a vanadium compound is employed, normal dosage amounts may vary from about 10 ng/kg up to about 100 mg/kg of mammal body weight or more per day, preferably about 1 g/kg/day to 10 mg/kg/day, depending upon the route of administration. Guidance as to particular dosages and methods of delivery is provided in the literature; see, for example, U.S. Pat. No. 4,657,760; 5,206,344 or 5,225,212. It is anticipated that different formulations will be effective for different treatments and different disorders, and that administration intended to treat a specific bone site or condition, may necessitate delivery in a manner different from that for another site or condition.

The formulations used herein may also contain more than one active compound as necessary for the particular indication being treated, preferably those with complementary activities that do not adversely affect each other. Alternatively, or in addition, the formulation may comprise a cytotoxic agent, cytokine or growth inhibitory agent. Such molecules are present in combinations and amounts that are effective for the intended purpose.

Therapeutic formulations of vanadium compounds in the vanadium delivery systems employable in the methods of the present invention are prepared for storage by mixing the vanadium compound having the desired degree of purity with optional pharmaceutically acceptable carriers, excipients, or stabilizers (Remington's Pharmaceutical Sciences 16th edition, Osol, A. Ed. (1980)). Such therapeutic formulations can be in the form of lyophilized formulations or aqueous solutions. Acceptable biocompatible carriers, excipients, or stabilizers are nontoxic to recipients at the dosages and concentrations employed, and may include buffers, for example, phosphate, citrate, and other organic acids; antioxidants including ascorbic acid and methionine; preservatives (e.g., octadecyldimethylbenzyl ammonium chloride; hexamethonium chloride; benzalkonium chloride, benzethonium chloride; phenol, butyl or benzyl alcohol; alkyl parabens, for example, methyl or propyl paraben; catechol; resorcinol; cyclohexanol; 3-pentanol; and m-cresol); low molecular weight (less than about 10 residues) polypeptides; proteins, for example, serum albumin, gelatin, or immunoglobulins; hydrophilic polymers, for example, polyvinylpyrrolidone; amino acids, for example, glycine, glutamine, asparagine, histidine, arginine, or lysine; monosaccharides, disaccharides, and other carbohydrates including glucose, mannose, dextrins, or hyaluronan; chelating agents, for example, EDTA; sugars, for example, sucrose, mannitol, trehalose or sorbitol; salt-forming counter-ions, for example, sodium; metal complexes (e.g., Zn-protein complexes); and/or non-ionic surfactants, for example, TWEEN™, PLURONICS™ or polyethylene glycol (PEG).

In order for the formulations to be used for in vivo administration, they must be sterile. The formulation may be readily rendered sterile by filtration through sterile filtration membranes, prior to or following lyophilization and reconstitution. The therapeutic formulations herein preferably are placed into a container having a sterile access port, for example, an intravenous solution bag or vial having a stopper pierceable by a hypodermic injection needle.

The formulations used herein may also contain more than one active compound as necessary for the particular indication being treated, preferably those with complementary activities that do not adversely affect each other. Alternatively, or in addition, the formulation may comprise a cytotoxic agent, cytokine or growth inhibitory agent. Such molecules are present in combinations and amounts that are effective for the intended purpose.

Optionally, the vanadium delivery system includes a bioactive bone agent in addition to vanadium insulin-mimetic agent. Preferably, the bioactive bone agent is selected from peptide growth factors (e.g., IGF (1, 2), PDGF (AA, AB, BB), BMPs, FGF (1-20), TGF-beta (1-3), aFGF, bFGF, EGF, and VEGF), anti-inflammatory factors (e.g., anti-TNFα, soluble TNF receptors, IL1ra, soluble IL1 receptors, IL4, IL-10, and IL-13), pro-inflammatory factors, inhibitors of apoptosis, MMP inhibitors and bone catabolic antagonists (e.g., bisphosphonates and osteoprotegerin).

The vanadium may also be entrapped in microcapsules prepared, for example by coacervation techniques or by interfacial polymerization, for example, hydroxymethylcellulose or gelatin-microcapsules and poly-(methylmethacrylate) microcapsules, respectively. Such preparations can be administered in colloidal drug delivery systems (for example, liposomes, albumin microspheres, microemulsions, nano-particles and nanocapsules) or in macroemulsions. Such techniques are disclosed in Remington's Pharmaceutical Sciences, 16th Edition (or newer), Osol A. Ed. (1980).

Optionally, vanadium in the vanadium delivery systems includes a porous calcium phosphate, non-porous calcium phosphate, hydroxyapatite, tricalcium phosphate, tetracalcium phosphate, calcium sulfate, calcium minerals obtained from natural bone, inorganic bone, organic bone, or a combination thereof.

Where sustained-release or extended-release administration of vanadium in the vanadium delivery systems is desired, microencapsulation is contemplated. Microencapsulation of recombinant proteins for sustained release has been successfully performed with human growth hormone (rhGH), interferon-α, -β, -γ (rhIFN-α, -β, -γ), interleukin-2, and MN rgp120. (Johnson et al., *Nat. Med.*, 1996, 2:795-799; Yasuda, *Biomed. Ther.*, 1993, 27:1221-1223; Hora et al., *Bio/Technology*, 1990, 8:755-758; Cleland, "Design and Production of Single Immunization Vaccines Using Polylactide Polyglycolide Microsphere Systems" in Vaccine Design: The Subunit and Adjuvant Approach, Powell and Newman, eds., Plenum Press: New York, 1995, pp. 439-462; WO 97/03692, WO 96/40072, WO 96/07399 and U.S. Pat. No. 5,654,010).

Suitable examples of sustained-release preparations include semipermeable matrices of solid hydrophobic polymers containing the vanadium in the vanadium delivery systems, which matrices are in the form of shaped articles, e.g. films, or microcapsules. Examples of sustained-release matrices include one or more polyanhydrides (e.g., U.S. Pat. Nos. 4,891,225 and 4,767,628), polyesters, for example, polyglycolides, polylactides and polylactide-co-glycolides (e.g., U.S. Pat. Nos. 3,773,919; 4,767,628; and 4,530,840; Kulkarni et al., *Arch. Surg.*, 1996, 93:839), polyamino acids, for example, polylysine, polymers and copolymers of polyethylene oxide, polyethylene oxide acrylates, polyacrylates, ethylene-vinyl acetates, polyamides, polyurethanes, polyorthoesters, polyacetylnitriles, polyphosphazenes, and polyester hydrogels (for example, poly(2-hydroxyethyl-methacrylate), or poly(vinylalcohol)), cellulose, acyl substituted cellulose acetates, non-degradable polyurethanes, polystyrenes, polyvinyl chloride, polyvinyl fluoride, poly(vinylimidazole), chlorosulphonated polyolefins, polyethylene oxide, copolymers of L-glutamic acid and .gamma.-ethyl-L-glutamate, non-degradable ethylene-vinyl acetate, degradable lactic acid-glycolic acid copolymers, for example, the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release for over 100 days, certain hydrogels release proteins for shorter time periods. Additional non-biodegradable polymers which may be employed are polyethylene, polyvinyl pyrrolidone, ethylene vinylacetate, polyethylene glycol, cellulose acetate butyrate and cellulose acetate propionate.

Alternatively, sustained-release formulations may be composed of degradable biological materials, for example, bio-erodible fatty acids (e.g., palmitic acid, stearic acid, oleic acid, and the like). Biodegradable polymers are attractive drug formulations because of their biocompatibility, high responsibility for specific degradation, and ease of incorporating the active drug into the biological matrix. For example, hyaluronic acid (HA) may be crosslinked and used as a swellable polymeric delivery vehicle for biological materials. (U.S. Pat. No. 4,957,744; Valle et al., *Polym. Mater. Sci. Eng.*, 1991, 62:731-735). HA polymer grafted with polyethylene glycol has also been prepared as an improved delivery matrix which reduced both undesired drug leakage and the denaturing associated with long term storage at physiological conditions. (Kazuteru, M., J. *Controlled Release*, 1999, 59:77-86). Additional biodegradable polymers which may be used are poly(caprolactone), polyanhydrides, polyamino acids, polyorthoesters, polycyanoacrylates, poly(phosphazines), poly(phosphodiesters), polyesteramides, polydioxanones, polyacetals, polyketals, polycarbonates, polyorthocarbonates, degradable and nontoxic polyurethanes, polyhydroxylbutyrates, polyhydroxyvalerates, polyalkylene oxalates, polyalkylene succinates, poly(malic acid), chitin, and chitosan.

Alternatively, biodegradable hydrogels may be used as controlled-release materials for the vanadium compounds in the vanadium delivery systems. Through the appropriate choice of macromers, membranes can be produced with a range of permeability, pore sizes and degradation rates suitable for different types of vanadium compounds in the vanadium delivery systems.

Alternatively, sustained-release delivery systems for vanadium in the vanadium delivery systems can be composed of dispersions. Dispersions may further be classified as either suspensions or emulsions. In the context of delivery vehicles for a vanadium compound, suspensions are a mixture of very small solid particles which are dispersed (more or less uniformly) in a liquid medium. The solid particles of a suspension can range in size from a few nanometers to hundreds of microns, and include microspheres, microcapsules and nanospheres. Emulsions, on the other hand, are a mixture of two or more immiscible liquids held in suspension by small quantities of emulsifiers. Emulsifiers form an interfacial film between the immiscible liquids and are also known as surfactants or detergents. Emulsion formulations can be both oil in water (o/w) wherein water is in a continuous phase while the oil or fat is dispersed, as well as water in oil (w/o), wherein the oil is in a continuous phase while the water is dispersed. One example of a suitable sustained-release formulation is disclosed in WO 97/25563. Additionally, emulsions for use with a vanadium compound in the present invention include multiple emulsions, microemulsions, microdroplets and liposomes. Microdroplets are unilamellar phospholipid vesicles that consist of a spherical lipid layer with an oil phase inside. (E.g., U.S. Pat. No. 4,622,219 and U.S. Pat. No. 4,725,442). Liposomes are phospholipid vesicles prepared by mixing water-insoluble polar lipids with an aqueous solution.

Alternatively, the sustained-release formulations of vanadium in the vanadium delivery systems may be developed using poly-lactic-co-glycolic acid (PLGA), a polymer exhibiting a strong degree of biocompatibility and a wide range of biodegradable properties. The degradation products of PLGA, lactic and glycolic acids, are cleared quickly from the human body. Moreover, the degradability of this polymer can be adjusted from months to years depending on its molecular weight and composition. For further information see Lewis, "Controlled Release of Bioactive Agents from Lactide/Glycolide polymer," in Biodegradable Polymers as Drug Delivery Systems, M. Chasin and R. Langeer, eds. (Marcel Dekker: New York, 1990), pp. 1-41.

The route of administration of "local vanadium" via "insulin mimetic delivery system" is in accordance with known methods, e.g. via immediate-release, controlled-release, sustained-release, and extended-release means. Preferred modes of administration for the insulin-mimetic delivery system include injection directly into afflicted bone site and areas adjacent and/or contiguous to these site or surgical implantation of insulin-mimetic delivery system directly into afflicted bone sites and area adjacent and/or contiguous to these site. This type of system may allow temporal control of release as well as location of release as stated above.

As an illustrated example, Vanadium may be continuously administered locally to a site via a delivery pump. In one embodiment, the pump is worn externally (in a pocket or on the belt) and attached to the body with a long, thin, and flexible plastic tubing that has a needle or soft cannula (thin plastic tube), and the cannula or needle is inserted and then left in place beneath the skin. The needle or cannula and tubing can be changed, for example, every 48 to 72 hours. The pump would store the vanadium in a cartridge and release it based on the optimal delivery rate. Optionally, the pump is programmed to give a small dose of a drug continuously through the day and night, which in certain circumstances may be preferred.

The present invention may prove effective at treating both non-unions and delayed unions. Because up to 10% of the 6.2 million fractures sustained annually proceed to delayed union and non-union (Praemer, A. and Rice D., *Am. Acad. Orthop. Surg.*, 1992, 85-124), the present invention may find wide applications.

In one preferred embodiment, the present invention can be used for treating military injuries. In the recent United States conflicts, significant improvements in personal body armor have led to fewer casualties. While this advancement in personal protection has reduced the number of mortalities, the morbidity of war, specifically a dramatically larger portion of battle-related injuries, has occurred in the extremities. Depending upon the level of energy, extremity fracture may range from simple closed fracture to large segmental defects with a significant bone and soft tissue loss evident. Battle-related fractures have very high complication rates (47% in one study) with delayed union and non-union in 31% of all the fractures followed (Pukljak D., *J. Trauma.*, 1997, 43(2):275-282). Many of these fractures occur in the extremities. Bullet wounds are often severe due to the large amount of kinetic energy expended on the bone surface.

Current simple and comminuted fracture treatment relies upon restoring the bone's anatomy and stabilizing the fractured bone until the body is able to heal the fracture with newly produced bone. Adjuncts to this basic procedure such as a method to significantly enhance bone regeneration and while maintaining appropriate blood flow and preventing infection have the potential to revolutionize this field. Osseous agents such as vanadium may enhance fracture callus strength by exploiting the healing responsiveness of insulin pathways. Localized therapy of this non-protein agent has a minimal possibility of infection or systemic consequences associated with systemic treatments.

The high complication rate of severe military injuries with delayed union and non-unions parallels the observations seen in the civilian population, who have risk factors for impaired bone healing. Risk factors include smoking, old age, steroid use, certain pharmaceuticals (i.e. anti-cancer drugs) and diabetes mellitus (DM). Treatment method suitable for the impaired osseous healing associated with high-risk populations can also be used to accelerate fracture healing in the normal, young, healthy soldiers.

In another preferred embodiment, the present invention may find wide application in sports medicines to treat a variety of fractures, including fatigue fractures and acute sports-related fractures. Acute fractures occurring during athletics result from overloading bone (boot top tibial fractures in skiing) or from ligament to tendon avulsion (tibial tubercle avulsion during long jumping). High school football injuries alone account for over 38,000 annual fractures (DeCoster, T. A., et al., *Iowa Orthop. J.*, 1994, 14:81-84). Sports fractures include, but are not limited to, tibial (49%), femoral (7%), and tarsal (25%) fractures which may differ depending on the individual and cause of injury (DeCoster, T. A., et al., *Iowa Orthop. J.*, 1994, 14:81-84). The present work examined a mid-diaphyseal fracture pattern, but it is likely that other fracture patterns would heal in the same fashion.

In yet another embodiment, the present invention may find wide application in veterinary medicines to treat a variety of fractures in a mammalian animal, including but not limited to, horses, dogs, cats, or any other domestic or wild mammalian animals. A particular useful application may be found, for example, in treating an injured race horse.

The following non-limiting examples illustrate certain aspects of the invention.

EXAMPLES

Materials and Methods

The BB Wistar Rat Model
Animal Source and Origin

Diabetic Resistance (DR) BB Wistar rats used in the study were obtained from a breeding colony at UMDNJ-New Jersey Medical School (NJMS). The rats were housed under controlled environmental conditions and fed ad libitum.

Diabetic Resistant BB Wistar Rats

A total of 86 DR BB Wistar rats were utilized in the study. Twenty samples were excluded from the study, fifteen due to inappropriately fractured condyles and five due to movement in potting during testing. The remaining 66 animals were used for mechanical testing, distributed amongst the control saline (n=6), calcium sulfate buffer (n=9), 0.25 mg/kg VAC (n=6), 0.5 mg/kg VAC (n=6), 1.5 mg/kg VAC (n=15), 3 mg/kg VAC (n=13), 0.25 mg/kg VAC with calcium sulfate carrier (n=6), and 1.5 mg/kg VAC with calcium sulfate carrier (n=5) groups. At sacrifice, 2 ml of whole blood was collected and glucose and percent glycosylated hemoglobin (% HbAlc) levels were determined using a glycosylated hemoglobin kit (Bayer HealthCare, Sunnyvale, Calif.). Glycosylated hemoglobin is a time-averaged measure of blood glucose control and can be twice as high in patients with poor blood glucose control when compared to normal patients.

Closed Femoral Fracture Model

Surgery was performed in DR animals between ages 80 and 120 days, using a closed mid-diaphyseal fracture model, on the right femur as described previously.

Figure 1:
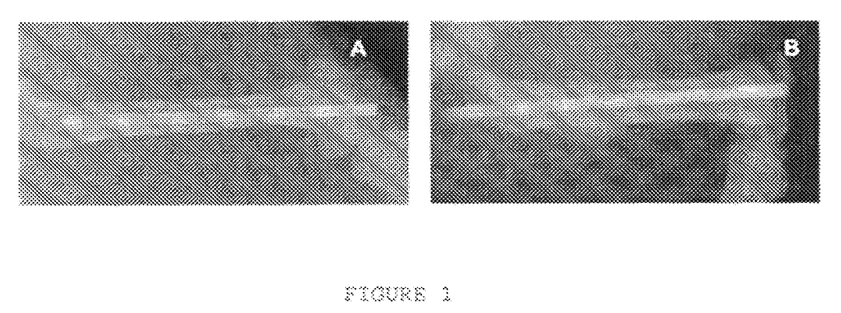
FIG. 1 shows post-operative X-rays: Representative x-rays taken immediately post-operative where (A) Einhorn model and (B) model are used in this work. (Note in (B) the Kirschner wire is going through the trochanter, which helps to stabilize the fracture site and prevent the migration of the Kirschner wire).

General anesthesia was administrated by intraperitoneal (IP) injection of ketamine (60 mg/kg) and xylazine (8 mg/Kg). The right leg of each rat was shaved and the incision site was cleansed with Betadine and 70% alcohol. An approximately 1 cm medial, parapatellar skin incision was made over the patella. The patella was dislocated laterally and the interchondylar notch of the distal femur was exposed. An entry hole was made with an 18 gauge needle and the femur was reamed with the 18 gauge needle. A Kirschner wire (316LVM stainless steel, 0.04 inch diameter, Small Parts, Inc., Miami Lakes, Fla.) was inserted the length of the medullary canal, and drilled through the trochanter of the femur. The Kirschner wire was cut flush with the femoral condyles. After irrigation, the wound was closed with 4-0 vicryl resorbable suture. A closed midshaft fracture was then created unilaterally with the use of a three-point bending fracture machine. X-rays were taken to determine whether the fracture is of acceptable configuration. An appropriate fracture is an approximately mid-diaphyseal, low energy, transverse fracture (FIG. 1). The rats were allowed to ambulate freely immediately post-fracture. This closed fracture model is commonly used to evaluate the efficacy of osseous wound healing devices and drugs.

Experimental Treatments

Local Vanadium Delivery

A 0.1 ml solution of Vanadium (Vanadyl acetylacetonate (VAC), Sigma Aldrich, St. Louis, Mo.) was injected into the intramedullary canal prior to fracture mixed with sterile water at concentrations of 0.725 mg VAC/ml water (extra low dose), 1.45 mg VAC/ml water (lowered low dose), 4.35 mg VAC/ml water (low dose), and 8.7 mg VAC/ml water (high dose). The extra low dose correlated to a dose of 0.25 mg/ml, the lowered low dose correlated to 0.5 mg/kg, the low dose correlated to 1.5 mg/kg and high dose correlated to 3.0 mg/kg. The analysis of low dose and high dose VAC in combination with calcium sulfate ($CaSO_4$) hemihydrate (J. T. Baker) will be described below.

Local Vanadium Treatment Using $CaSO_4$ as a Carrier

Two grams of $CaSO_4$ were placed in glass vials. The vials were placed in a mechanical convection oven and sterilized at 196° C. for 6 hours.

To prepare the $CaSO_4$-VAC mixture, 0.8 g of $CaSO_4$ was mixed with 400 µl of saline or the respective VAC solutions for one minute at room temperature. The mixture was packed into the barrel of a 1 cc sterile syringe and pushed down to the open orifice of the syringe barrel by insertion of the syringe plunger. After attaching an 18-gauge sterile needle to the syringe barrel, 0.1 ml volume of the mixture was directly injected into the rat femoral canal (non-diabetic BB Wistar rat) prior to Kirschner wire insertion and fracture.

Four experimental groups were used:
(1) Saline Control (0.9% NaCl): 0.1 ml of saline was injected into the intramedullary canal of the right femur prior to the Kirschner wire insertion and fracture.
(2) Calcium Sulfate Buffer Control: 0.1 ml of the $CaSO_4$-Saline mixture was injected into the intramedullary canal of the right femur prior to Kirschner wire insertion and fracture.
(3) 0.25 mg/kg Local VAC+Carrier: 0.1 ml of the $CaSO_4$-VAC (Vanadyl acetylacetonate (VAC), Sigma Aldrich, St. Louis, Mo.) mixture was injected into the intramedullary canal of the right femur prior to Kirschner wire insertion and fracture.
(4) 1.25 mg/kg Local VAC+Carrier: 0.1 ml of the $CaSO_4$-VAC (Vanadyl acetylacetonate (VAC), Sigma Aldrich, St. Louis, Mo.) mixture was injected into the intramedullary canal of the right femur prior to Kirschner wire insertion and fracture.

Glycosylated Hemoglobin (HbAlc)

Glycosylated hemoglobin (HbAlc) is formed by the non-enzymatic reaction between glucose and the globin chains of hemoglobin. Specifically, glucose forms a non-covalent bond with an amine group found in the hemoglobin molecule. This reaction occurs continuously throughout the life-cycle of the red blood cell and, therefore, becomes a measure of average blood glucose levels during the life of the cell. HbAlc has been accepted as a time-averaged measure of blood glucose control and can be twice as high in patients with poor blood glucose control when compared to normal patients.

Blood was collected from rats at sacrifice by cardiac puncture. Approximately 2 ml of whole blood was collected and the percent glycosylated hemoglobin (% HbAlc) was determined using a glycosylated hemoglobin kit (Bayer HealthCare, Sunnyvale, Calif.) as per the manufacturer's instructions.

Mechanical Testing

Figure 3:
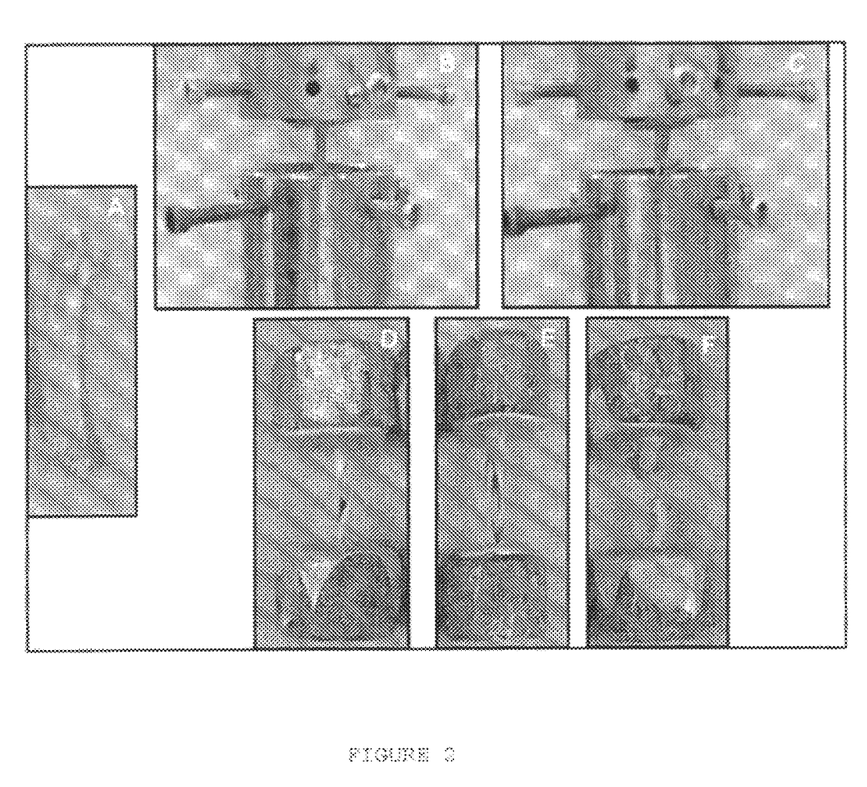
FIG. 3 shows x-ray photographs of femurs of saline vs. VAC after 4 weeks.

X-rays were taken at 4 weeks to determine the extent of healing of the fractures (FIG. 3).

Fractured and contralateral femora were resected at 4 and 5 weeks post-fracture. Femora were cleaned of soft tissue and the intramedullary rod was removed. Samples were wrapped in saline (0.9% NaCl) soaked gauze and stored at −20° C. Prior to testing, all femora were removed from the freezer and allowed to thaw to room temperature for three to four hours. The proximal and distal ends of the fractured and contralateral femora were embedded in ¾ inch square nuts with Field's Metal, leaving an approximate gauge length of 12 mm (FIG. 2). After measuring callus and femur dimensions, torsional testing was conducted using a servohydraulics machine (MTS Systems Corp., Eden Prairie, Minn.) with a 20 Nm reaction torque cell (Interface, Scottsdale, Ariz.) and tested to failure at a rate of 2.0 deg/sec. The maximum torque to failure and angle to failure were determined from the force to angular displacement data.

Peak torque to failure ($T_{max}$), torsional rigidity (TR), effective shear modulus (SM), and effective torsional shear stress (SS) were calculated through standard equations. $T_{max}$ and TR are considerd extrinsic properties while SM and SS are considered intrinsic properties. $T_{max}$ was defined as the point where an increase in angular displacement failed to produce any further increase in torque. TR is a function of the torque to failure, gauge length (distance of the exposed femur between the embedded proximal and distal end) and angular displacement. SS is a function of the torque to failure, maximum radius within the mid-diaphyseal region and the polar moment of inertia. The polar moment of inertia was calculated by modeling the femur as a hollow ellipse. Engesaeter et al. (*Acta Orthop. Scand.*, 1978, 49(6):512-518) demonstrated that the calculated polar moment of inertia using the hollow ellipse model differed from the measured polar moment of inertia by only 2 percent (Engesaeter et al., *Acta Orthop. Scand.*, 1978, 49(6):512-518).

In order to compare the biomechanical parameters between different groups, the data was normalized by dividing each fractured femur value by its corresponding intact, contralateral femur value (FIG. 2). Normalization was used to minimize biological variability due to differences in age and weight among rats.

Figure 4:
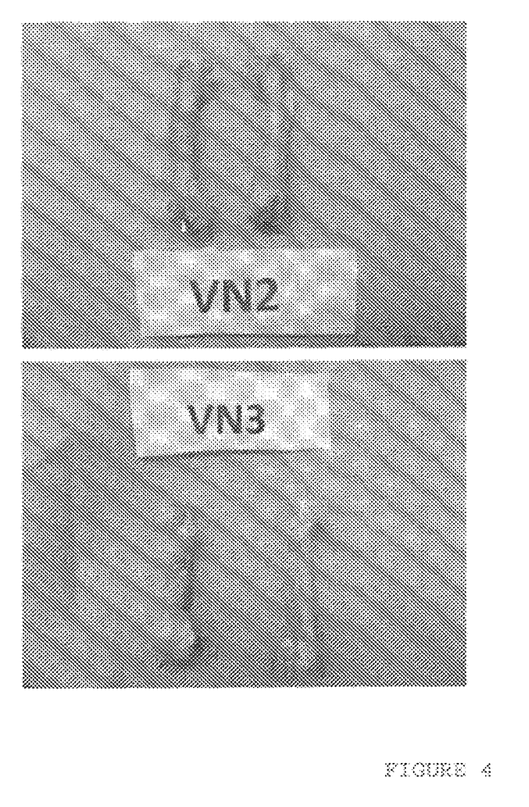
FIG. 4 shows post-surgery bones where VN2 and VN3 represent two sets of VAC-treated femurs harvested 4 weeks post-surgery (Left: Fractured Femur; Right: Intact Femur).
Figure 6:
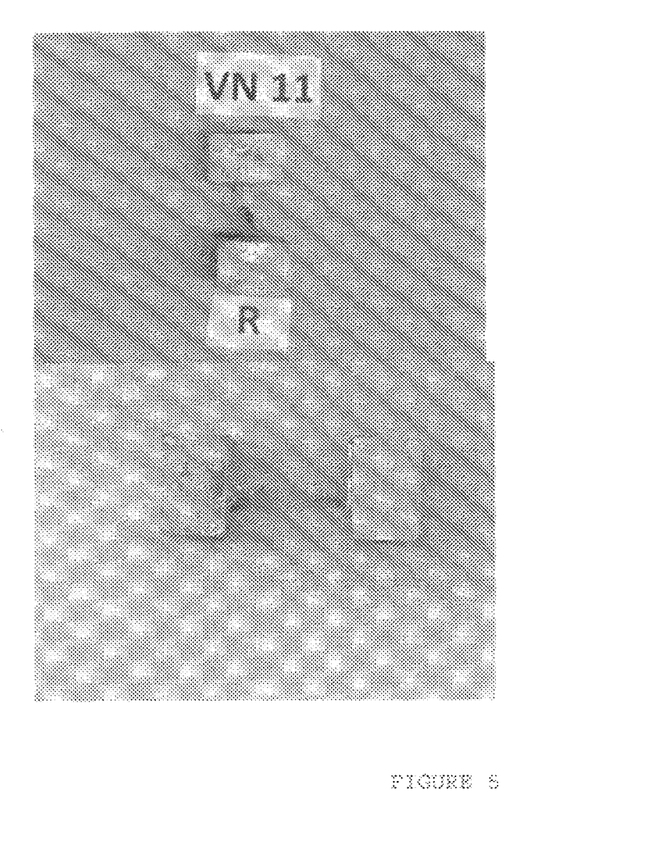

In addition to the biomechanical parameters determined through torsional testing, the mode of failure can also provide substantial information. The mode of torsional failure as determined by gross inspection provided an indication as to the extent of healing (FIG. 4). A spiral failure in the mid-diaphyseal region indicated a complete union while a transverse failure through the fracture site indicated a nonunion. A combination spiral/transverse failure indicated a partial union (FIG. 5).

Data and Statistical Analysis

Analysis of variance (ANOVA) was performed followed by Holm-Sidak post-hoc tests to determine differences (SigmaStat 3.0, SPSS Inc., Chicago, Ill.). A P value less than 0.05 was considered statistically significant.

Results

General Health

In this biomechanical testing experiment, animals among treatment groups were age matched. There was no statistical difference among treatment groups in percent weight gain from the time of surgery indicating that vanadium injected locally into the intramedullary canal had no effect on metabolism (Table 1). Blood glucose levels and age at surgery showed a significant difference between the high dose and saline groups (Table 2) however, the clinical relevance of this observation is difficult to ascertain since this range is within the normoglycemic value of Non-DM rats. These fluctuations may be a result of the small sample size and variations based on diet.

All animals were grouped within the same age within 40 days (80-120 days). The average difference in age between groups was less than 12 days between the high dose and saline treated groups, and less than three days between low dose and control treated groups. Such a small age difference within this phase is an unlikely factor to cause any major variances in healing rates.

TABLE 1

General Health of Non-DM BB Wistar Rats: Local Vanadium (VAC) Delivery without a Carrier (4 Week Mechanical Testing)

|  | Blood Glucose (mg/dl)* Pre-Surgery | Age At Surgery | % Weight gain |
|---|---|---|---|
| Saline (n = 5) | 81.7 ± 4.3 (day 1) | 99.0 ± 1.0[b] | 3.5 ± 2.3 |
| Low Dose (n = 6) | 95.1 ± 6.1 | 96.3 ± 7.5 | 7.7 ± 6.5 |
| High Dose (n = 5) | 107.6 ± 19.1[a] | 88.2 ± 5.0 | 8.1 ± 7.2 |

The data represents average values ± standard deviation
[a]represents values significantly greater than the saline group; p = 0.003
[b]represents values significantly greater than the high dose group; p = 0.008

Mechanical Testing Results

The effect of local vanadium therapy on healing of femur fractures in normal (non-diabetic) rats was measured by torsional mechanical testing. At 4 weeks post-fracture, rats treated with between 1.5 mg/kg and 3 mg/kg VAC displayed improved mechanical properties of the fractured femora compared to the untreated saline group. The maximum torque to failure (P<0.05), maximum torsional rigidity (P<0.05), effective shear stress (P<0.05), and effective shear modulus (P<0.05) were all significantly increased compared to the untreated group (Table 2). Maximum torque to failure and maximum torsional rigidity were also significantly increased (P<0.05) for the 0.5 mg/kg VAC compared to the untreated saline group. When the mechanical parameters of the fractured femora were normalized to the intact, contralateral femora, percent torque to failure (P<0.05), percent maximum torsional rigidity (P<0.05 HD), and percent effective shear modulus (P<0.05) were significantly greater for several of the local vanadium treated groups when compared to the saline group. (Table 2).

At 5 weeks post-fracture, rats treated with 1.5 mg/kg displayed improved mechanical properties of the fractured femora compared to the untreated saline group and the 3 mg/kg VAC treated group. The maximum torque to failure (P<0.05), maximum torsional rigidity (P<0.05) were all significantly increased compared to the untreated group. The 1.5 mg/kg VAC group also demonstrated a significantly higher maximum torque to failure (P<0.05) compared to the 3 mg/kg VAC group (Table 3). When the mechanical parameters of the fractured femora were normalized to the intact, contralateral femora, although several parameters approached significance, none were determined to be significant (Table 3).

At 4 weeks post-fracture, rats treated with 0.25 mg/kg VAC and a calcium sulfate carrier displayed improved mechanical properties of the fractured femora compared to the untreated saline group and the calcium sulfate buffer group. The maximum torque to failure (P<0.05), and effective shear modulus (P<0.05) were both significantly increased compared to the untreated group, while the effective shear stress was significantly increased (P<0.05) for the 0.25 mg/kg VAC w/Calcium Sulfate group compared to the untreated saline, calcium sulfate buffer, and 1.5 mg/kg VAC w/Calcium Sulfate groups (Table 4). When the mechanical parameters of the fractured femora were normalized to the intact, contralateral femora, percent torque to failure (P<0.05), and percent effective shear modulus (P<0.05) were significantly greater for the 0.25 mg/kg VAC w/Calcium Sulfate group compared to the untreated saline, and calcium sulfate buffer groups (Table 2). Percent maximum torsional rigidity was significantly higher (P<0.05) for the 0.25 mg/kg VAC w/Calcium Sulfate group compared to the untreated saline group (Table 4).

To our knowledge, this is the first study to examine the effect of local vanadium treatment on fracture healing, quantified by mechanical testing. Our study demonstrated that local VAC treatment significantly improved the biomechanical parameters of fracture healing in normal animals (Tables 2-4).

At four weeks the average percent torque to failure of the fractured femora for both 1.5 mg/kg and 3.0 mg/kg doses with no carrier were significantly greater, with 3.0 mg/kg dose 1.93 times greater (79.0% of contralateral vs. 27.0%), and 1.19 times greater (59.0% of contralateral vs. 27.0%) compared to the untreated saline group. Percent maximum torsional rigidity values for both 1.5 mg/kg and 3.0 mg/kg doses were significantly greater, with 3.0 mg/kg dose 2.90 times greater (78.0% of contralateral vs. 20.0%), and 2.80 times greater (76.0% of contralateral vs. 20.0%) compared to the untreated saline group. Percent effective shear modulus values for both 1.5 mg/kg and 3.0 mg/kg doses were significantly greater, with high dose 4.75 times greater (23.0% of contralateral vs. 4.0%), and 4 times greater (20.0% of contralateral vs. 4.0%) compared to the untreated saline group. Percent effective shear stress values for the 3.0 mg/kg dose was significantly greater, 2 times greater (30.0% of contralateral vs. 10.0%), compared to the untreated saline group.

At four weeks with the introduction of an industry standard carrier (Calcium Sulfate), the average percent torque to failure of the fractured femora for the 0.25 mg/kg dose were significantly greater than both the untreated saline, 2.15 times greater (85.0% of contralateral vs. 27.0%) and Calcium Sulfate Buffer, 1.30 times greater (85.0% of contralateral vs. 37.0%) groups. Percent maximum torsional rigidity for the 0.25 mg/kg dose was significantly greater than the untreated saline, 4 times greater (100.0% of contralateral vs. 20.0%). Percent effective shear modulus values for the 0.25 mg/kg dose were significantly greater than both the untreated saline, 5 times greater (24.0% of contralateral vs. 4.0%) and Calcium Sulfate Buffer, 2.43 times greater (24.0% of contralateral vs. 7.0%) groups.

These results exemplify the incredible potential of local VAC treatment for non-diabetic fracture healing. They show that lower doses of VAC with a carrier may optimize its delivery, and its reduce effective dose. Further we show a near dose dependent response to VAC delivery, with higher doses leading to enhanced biomechanical parameters. At five weeks post fracture, it is clear that there is a limit to the effectiveness of vanadium compounds the highest dose tested in terms of callus size and bone remodeling (Table 4). An earlier study examining the effect of vanadium on mechanical strength of intact (non fractured) bone in non-diabetic and diabetic animals revealed that vanadium had no effect on bone homeostasis in non-diabetic animals (Facchini, D. M., et al., *Bone*, 2006, 38(3):368-377). The fracture healing pathway is different than the bone homeostasis pathway. This is likely the primary reason for conflicting results presented in both models. Other possibilities include different dosages and delivery methods in each study.

TABLE 2

Four weeks post-fracture mechanical testing with Vanadium (VAC) in normal rats

|  | Maximum Torque to failure (Nmm) | Maximum Torsional Rigidity (Nmm$^2$/rad) | Effective Shear Modulus (MPa) | Effective Shear Stress (MPa) |
| --- | --- | --- | --- | --- |
| Control (n = 6) | 161 ± 48 | 9,889 ± 4,719 | 258 ± 108 | 17 ± 4 |
| 0.25 mg/kg VAC (n = 6) | 227 ± 64 | 28,218 ± 9,107 | 878 ± 416 | 25 ± 9 |
| 0.5 mg/kg VAC (n = 6) | 362 ± 49 *,# | 45,877 ± 13,079 * | 1,107 ± 441 | 32 ± 13 |
| 1.5 mg/kg VAC (n = 6) | 329 ± 117 * | 34,526 ± 16,851 * | 2,454 ± 2,370 * | 69 ± 59 * |
| 3.0 mg/kg (n = 5) | 409 ± 43 *,# | 41,007 ± 11,236 * | 2,948 ± 1,218 * | 101 ± 18 *,#,& |

Fractured femur values normalized to the contralateral (intact) femur

|  | Percent maximum torque to failure | Percent maximum torsional rigidity | Percent Effective Shear Modulus | Percent Effective Shear Stress |
| --- | --- | --- | --- | --- |
| Control (n = 6) | 27 ± 18 | 20 ± 10 | 4 ± 2 | 10 ± 5 |
| 0.25 mg/kg VAC (n = 6) | 49 ± 14 | 67 ± 21 * | 14 ± 4 | 10 ± 3 |
| 0.5 mg/kg VAC (n = 6) | 72 ± 19 * | 103 ± 23 *,# | 16 ± 7 | 20 ± 11 |
| 1.5 mg/kg VAC (n = 6) | 59 ± 28 | 76 ± 28 * | 23 ± 12 * | 26 ± 16 |
| 3.0 mg/kg (n = 5) | 79 ± 12 * | 78 ± 10 * | 20 ± 11 * | 30 ± 12 *,# |

The data represents average values ± standard deviation
* Represent values statistically higher than control, p < 0.05 versus control.
Represent values statistically higher than Extra Low Dose, p < 0.05 versus Extra Low Dose.
& Represent values statistically higher than Lowered Low Dose, p < 0.05 versus Lowered Low Dose.

TABLE 3

Five weeks post-fracture mechanical testing with Vanadium (VAC) in normal rats

Fractured femur values

|  | Maximum Torque to failure (Nmm) | Maximum Torsional Rigidity (Nmm$^2$/rad) | Effective Shear Modulus (MPa) | Effective Shear Stress (MPa) |
| --- | --- | --- | --- | --- |
| Control (n = 6) | 295 ± 164 | 20,111 ± 10,944 | 1,060 ± 693 | 45 ± 28 |
| 1.5 mg/kg VAC (n = 9) | 471 ± 91*,# | 34,522 ± 8,347* | 2,026 ± 924 | 75 ± 26 |
| 3.0 mg/kg (n = 8) | 335 ± 89 | 37,496 ± 12,846* | 1,453 ± 683 | 43 ± 25 |

Fractured femur values normalized to the contralateral (intact) femur

|  | Percent maximum torque to failure | Percent maximum torsional rigidity | Percent Effective Shear Modulus | Percent Effective Shear Stress |
| --- | --- | --- | --- | --- |
| Control (n = 6) | 74 ± 42 | 80 ± 57 | 28 ± 29 | 31 ± 21 |
| 1.5 mg/kg VAC (n = 9) | 99 ± 17 | 103 ± 33 | 39 ± 26 | 47 ± 25 |
| 3.0 mg/kg (n = 8) | 64 ± 26 | 98 ± 28 | 23 ± 9 | 22 ± 11 |

The data represents average values ± standard deviation
*Represent values statistically higher than control, p < 0.05 versus control.
Represent values statistically higher than high dose, p < 0.05 versus high dose.

The results of four to five weeks post-fracture mechanical testing with VAC, in conjunction with $CaSO_4$ or alone, are listed in Table 2, Tables 3, and Table 4, respectively.

that local VAC application at the dosages tested, without a carrier may heal bone more than twice as rapidly as saline controls. This evidence opens up many future applications to

TABLE 4

Four weeks post-fracture mechanical testing with VAC and $CaSO_4$ in normal rats

| | Maximum Torque to failure (Nmm) | Maximum Torsional Rigidity (Nmm$^2$/rad) | Effective Shear Modulus (MPa) | Effective Shear Stress (MPa) |
|---|---|---|---|---|
| Control (n = 6) | 161 ± 48 | 9,889 ± 4,719 | 258 ± 108 | 17 ± 4 |
| $CaSO_4$ Buffer (n = 9) | 241 ± 172 | 25,684 ± 20,795 | 680 ± 623 | 23 ± 16 |
| 0.25 mg/kg VAC and $CaSO_4$ Carrier (n = 6) | 430 ± 133 * | 31,138 ± 11,518 | 1,178 ± 484 * | 55 ± 21 *,#,& |
| 1.5 mg/kg VAC and $CaSO_4$ Carrier (n = 5) | 322 ± 157 | 26,302 ± 17,974 | 637 ± 395 | 29 ± 15 |

Fractured femur values normalized to the contralateral (intact) femur

| | Percent maximum torque to failure | Percent maximum torsional rigidity | Percent Effective Shear Modulus | Percent Effective Shear Stress |
|---|---|---|---|---|
| Control (n = 6) | 27 ± 18 | 20 ± 10 | 4 ± 2 | 10 ± 5 |
| $CaSO_4$ Buffer (n = 9) | 37 ± 30 | 47 ± 47 | 7 ± 7 | 9 ± 6 |
| 0.25 mg/kg VAC and $CaSO_4$ Carrier (n = 6) | 85 ± 24 *,# | 100 ± 49 * | 24 ± 10 *,# | 18 ± 9 |
| 1.5 mg/kg VAC and $CaSO_4$ Carrier (n = 5) | 64 ± 30 | 69 ± 47 | 15 ± 8 | 10 ± 7 |

The data represents average values ± standard deviation
* Represent values statistically higher than control, $p < 0.05$ versus control.
Represent values statistically higher than $CaSO_4$ Buffer, $p < 0.05$ versus $CaSO_4$ Buffer.
& Represent values statistically higher than Low Dose and $CaSO_4$ Carrier, $p < 0.05$ versus Low Dose and $CaSO_4$ Carrier.

The insulin mimetic strategy of the present invention is further illustrated by comparison of the mechanical testing parameters of bone fracture healing of the femur in treatment of normal and diabetic subjects (Table 5), which shows that the 6-week values of the mechanical parameters are very low for the diabetic subjects but when the VAC was used at low dosages, these values increased substantially to values observed in normal subject fracture healing and even exceeded the values of a bone fracture for a normal subject after the same period of time.

the use of VAC alone, or incorporated with a carrier as an option for fracture healing.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit

TABLE 5

Comparison of the mechanical testing parameters of bone fracture healing of the femur in normal, diabetic and diabetic rats treated with VAC/carrier after 6 weeks.

| | Maximum Torque to failure (Nmm) | Maximum Torsional Rigidity (Nmm$^2$/rad) | Effective Shear Stress (MPa) |
|---|---|---|---|
| diabetic control (n = 23)† | 154 ± 69 | 425 ± 259 | 3 ± 2 |
| 1.5 mg/kg VAC in diabetic (n = 3) | 410 ± 71 * | 43,089 ± 19,720 * | 98 ± 53 *,# |
| normal (n = 12) | 456 ± 66 * | 33,784 ± 11,849 * | 48 ± 16 * |

| Normalized to contralateral femur | Percent maximum torque to failure | Percent maximum torsional rigidity | Percent Effective Shear Stress |
|---|---|---|---|
| diabetic control (n = 23) | 27 ± 10 | 27 ± 15 | 8 ± 4 |
| 1.5 mg/kg VAC in diabetic (n = 3) | 85 ± 23 * | 136 ± 111 * | 33 ± 20 * |
| normal (n = 12) | 78 ± 15 * | 86 ± 29 | 28 ± 13 * |

The data represents average values ± standard deviation
* Represent values statistically higher than control, $p < 0.05$ versus control.
Represent values statistically higher than normal, $p < 0.05$ versus normal.
†The value of the numbers for diabetic control is obtained from three papers of Gandhi (Insulin: Bone 2005; PRP: Bone 2006 and Beam et al 2002 JOR). The values of 6 week normal group is an average of Gandhi's paper and Dave Paglia 6 week mechanical test saline animals.

The above data has indicated that local vanadium treatment is an effective method to treat fracture patients, in particular non-diabetic patients. Mechanical parameters and microradiography revealed demonstrated that bone has bridged at 4 weeks post fracture. Spiral fractures that occurred during mechanical testing reaffirm this phenomenon and suggest and script of the invention, and all such variations are intended to be included within the scope of the following claims.

What is claimed is:

1. A method of promoting bone injury healing in a patient in need thereof, comprising locally administering to the bone injury site of said patient a therapeutically effective amount of a composition sterilized for in vivo bone administration comprising an insulin-mimetic vanadium compound and a pharmaceutically suitable carrier for localized bone site delivery.

2. The method of claim 1, wherein said vanadium compound is selected from the group consisting of vanadyl acetylacetonate (VAC), vanadyl sulfate (VS), vanadyl 3-ethylacetyl-acetonate (VET), and bis(maltolato)oxovanadium (BMOV).

3. The method of claim 1, wherein said vanadium compound is vanadyl acetyl-acetonate (VAC).

4. The method of claim 1, wherein said vanadium compound is directly administered to the bone injury site.

5. The method of claim 1, wherein said bone site is afflicted with a condition selected from the group consisting of bone fracture, bone trauma, arthrodesis and a bone deficit condition associated with post-traumatic bone surgery, post-prosthetic joint surgery, post-plastic bone surgery, post-dental surgery, bone chemotherapy treatment, congenital bone loss, post traumatic bone loss, post-surgical bone loss, post infectious bone loss, allograft incorporation or bone radiotherapy treatment.

6. The method of claim 5, wherein said condition is selected from bone fractures, osseous defects, and delayed unions and non-unions.

7. The method of claim 1, wherein the method is used in conjunction with an allograft, autograft or orthopedic biocomposite.

8. The method according of claim 1, wherein said vanadium compound is locally administered by a bone graft biocomposite containing said vanadium compound.

9. The method of claim 8, wherein the bone graft composite is selected from the group consisting of autografts, allografts, xenografts, alloplastic grafts, and synthetic grafts.

10. The method of claim 1, wherein said method comprises co-administering a cytotoxic agent, cytokine or growth inhibitory agent with said vanadium compound.

11. The method of claim 1, wherein the method is used in conjunction with an external bone growth stimulator.

12. The method of claim 1, wherein the method comprises co-administering a bioactive bone agent with said vanadium compound.

13. The method of claim 12, wherein said bioactive bone agent is selected from the group consisting of peptide growth factors, anti-inflammatory factors, pro-inflammatory factors, inhibitors of apoptosis, MMP inhibitors, and bone catabolic antagonists.

14. The method of claim 13, wherein said peptide growth factor is selected from the group consisting of IGF (1,2), PDGF (AA, AB, BB), BMPs, FGF (1-20), TGF-beta (1-3), aFGF, bFGF, EGF, VEGF, parathyroid hormone (PTH), and parathyroid hormone-related protein (PTHrP).

15. The method of claim 13, wherein said anti-inflammatory factor is selected from the group consisting of anti-TNFα, soluble TNF receptors, IL1ra, soluble IL1 receptors, IL4, IL-10, and IL-13.

16. The method of claim 13, wherein said bone catabolic antagonist is selected from the group consisting of bisphosphonates, osteoprotegerin, and statins.

17. The method of claim 1, wherein said patient is a mammalian animal.

18. The method of claim 1, wherein said patient is a human.

19. The method of claim 1, wherein said patient is a non-diabetic human.

20. A method of promoting bone injury healing comprising locally administering to a bone injury site of a patient in need thereof a therapeutically effective amount of a composition sterilized for in vivo bone administration comprising an insulin-mimetic vanadium compound.

21. The method of claim 20, wherein said composition comprises at least one biocompatible carrier.

22. The method of claim 21, wherein said biocompatible carrier is selected from the group consisting of poly-lactic acid, poly-glycolic acid, and copolymers of poly-lactic acid and poly-glycolic acid.

23. The method of claim 21, wherein said biocompatible carrier comprises at least one biodegradable fatty acid or a metal salt thereof.

24. The method of claim 23, wherein said fatty acid, is selected from the group consisting of palmitic acid, stearic acid, oleic acid, myristic acid, and metal salts thereof.

25. The method of claim 21, wherein said biocompatible carrier comprises a salt selected from the group consisting of porous or non-porous calcium phosphates, porous or non-porous hydroxyapatites, porous or non-porous tricalcium phosphates, porous or non-porous tetracalcium phosphates, porous or non-porous calcium sulfates, and combinations thereof.

26. The method of claim 20, further comprising treating said patient with at least one procedure selected from the group consisting of bone autograft, bone allograft, autologous stem cell treatment, allogeneic stem cell treatment, chemical stimulation, electrical stimulation, internal fixation, and external fixation.

\* \* \* \* \*